United States Patent [19]

Peterson

[11] 4,175,597
[45] Nov. 27, 1979

[54] IRRIGATION SOLUTION DEVICE
[75] Inventor: James J. Peterson, Palatine, Ill.
[73] Assignee: The Kendall Company, Boston, Mass.
[21] Appl. No.: 820,512
[22] Filed: Aug. 1, 1977
[51] Int. Cl.² .............................................. B65B 3/32
[52] U.S. Cl. .................................... 141/23; 128/272;
141/27; 141/285; 141/381; 215/228
[58] Field of Search ....................... 128/272; 141/2, 18,
141/21, 22–27, 285, 309, 310, 378, 379, 380,
381, 24; 215/228, 232; 222/588, 589

[56] References Cited

U.S. PATENT DOCUMENTS

| | | | |
|---|---|---|---|
| Re. 7,419 | 12/1876 | Brower | 119/77 |
| Re. 8,018 | 12/1877 | Lindemann | 119/77 |
| Re. 8,219 | 5/1878 | Lindeman | 119/77 |
| 104,300 | 6/1870 | Grimes | 222/585 |
| 169,735 | 11/1875 | Schirmer | 222/585 |
| 809,891 | 1/1906 | Baldwin | 222/585 |
| 826,263 | 7/1906 | McCloskey | 222/585 |
| 856,077 | 6/1907 | Malick | 222/585 |
| 864,061 | 8/1907 | Baldwin | 211/69.2 |
| 886,161 | 4/1908 | Swan | 119/77 X |
| 897,148 | 8/1908 | Ramirez | 222/585 |
| 962,968 | 6/1910 | Malick | 222/585 |
| 1,048,344 | 12/1912 | Risbon | 222/585 |
| 1,226,821 | 5/1917 | Siever | 141/110 |
| 1,834,516 | 12/1931 | Dains | 119/77 |
| 2,324,020 | 7/1943 | Pinson | 119/77 |
| 2,413,647 | 12/1946 | Oldfield | 119/77 |
| 2,562,165 | 7/1951 | Baringer | 119/77 |
| 2,573,802 | 11/1951 | Mitchell | 119/77 |
| 2,845,963 | 8/1958 | Zackheim | 141/24 |
| 3,049,226 | 8/1962 | Schurr | 206/46 |
| 3,076,435 | 2/1963 | Seymour | 119/77 |
| 3,137,969 | 6/1964 | Sokel | 47/57.5 |
| 3,292,589 | 12/1966 | Williams | 119/77 |
| 3,301,220 | 1/1967 | Queen | 119/77 |
| 3,655,084 | 4/1972 | Willhaus et al. | 215/232 |
| 3,783,996 | 1/1974 | Gerard | 206/17.5 |

FOREIGN PATENT DOCUMENTS

| | | |
|---|---|---|
| 214896 | 5/1924 | United Kingdom . |
| 265969 | 8/1927 | United Kingdom . |
| 752750 | 7/1956 | United Kingdom . |
| 1117468 | 6/1968 | United Kingdom . |
| 1132887 | 11/1968 | United Kingdom . |
| 1165133 | 9/1969 | United Kingdom . |
| 1258845 | 12/1971 | United Kingdom . |
| 1485581 | 9/1977 | United Kingdom . |

OTHER PUBLICATIONS

"Catheter Irrigation Without Risk of Infection."

Primary Examiner—Frederick R. Schmidt
Attorney, Agent, or Firm—Powell L. Sprunger

[57] ABSTRACT

An irrigation solution device comprising, a syringe having a barrel, a container having a solution receiving chamber, and a barrier member extending from an upper portion of the container into the chamber. The barrier member has an inner end portion defining an opening communicating with the chamber, and defines a channel having a sufficiently large width to receive the barrel of the syringe and a sufficient length to substantially cover the syringe barrel when inserted into the channel. The device has a closure member to releasably close the channel from passage of air between the atmosphere and the chamber.

12 Claims, 9 Drawing Figures

U.S. Patent  Nov. 27, 1979  Sheet 1 of 2  4,175,597
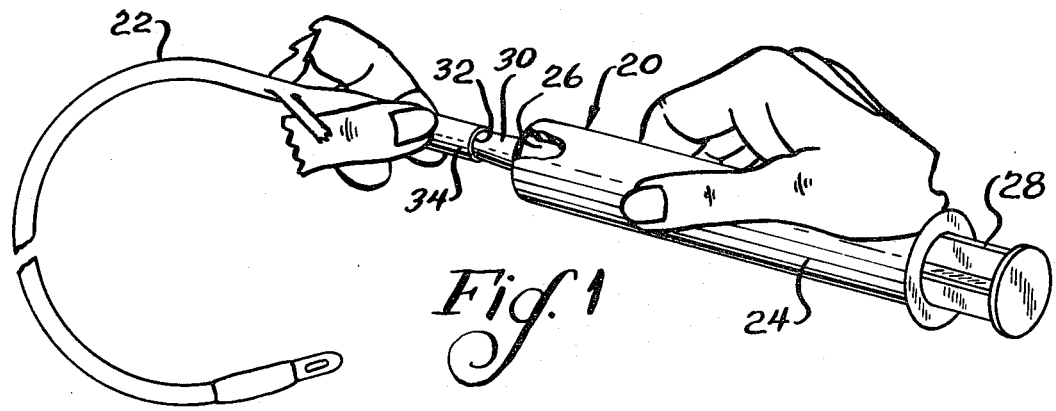
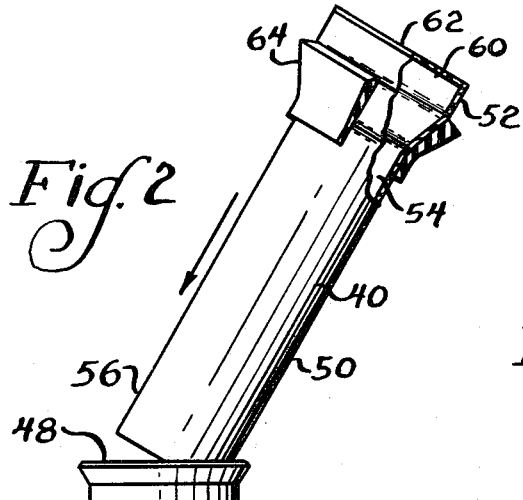
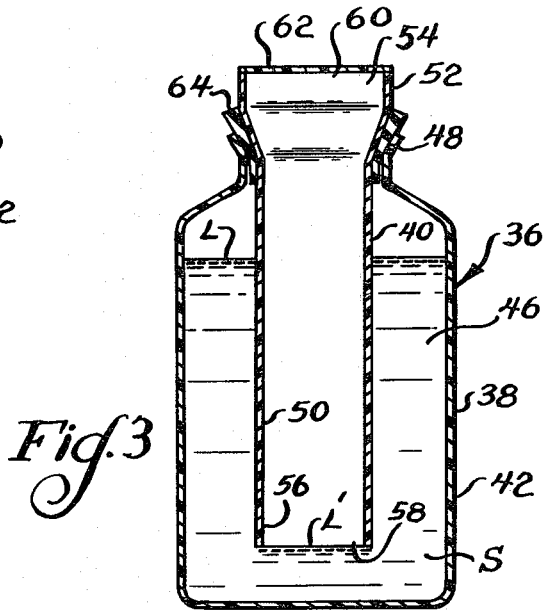
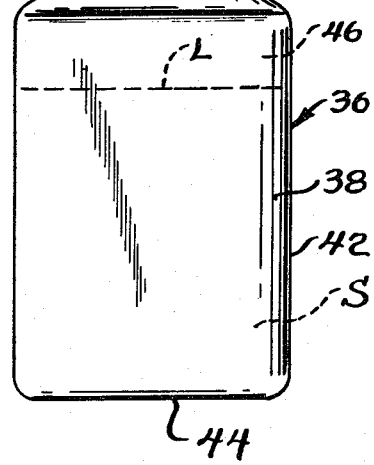
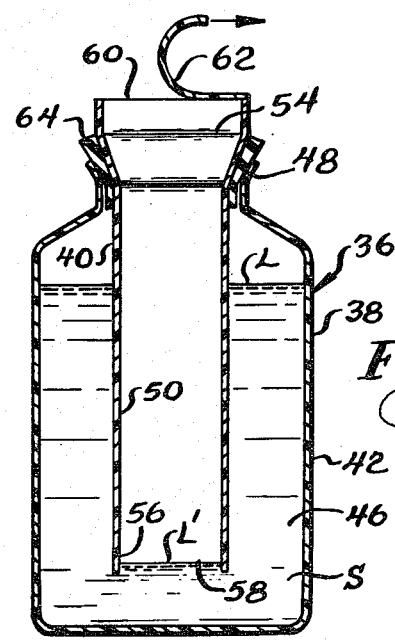

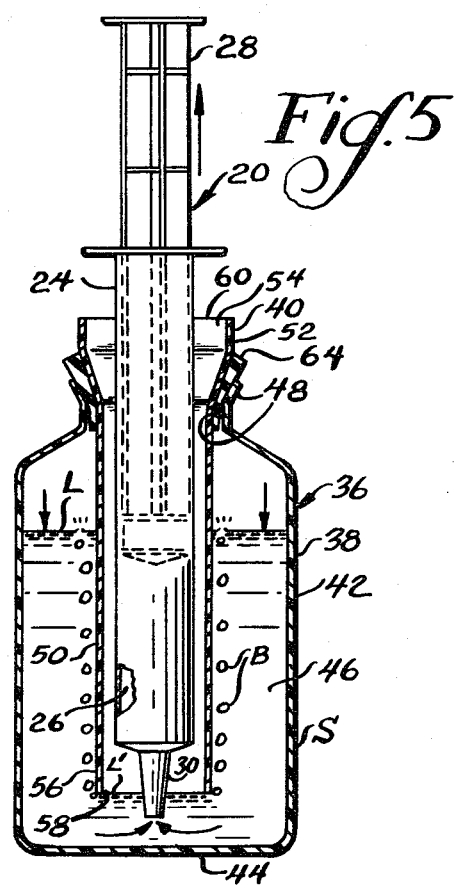
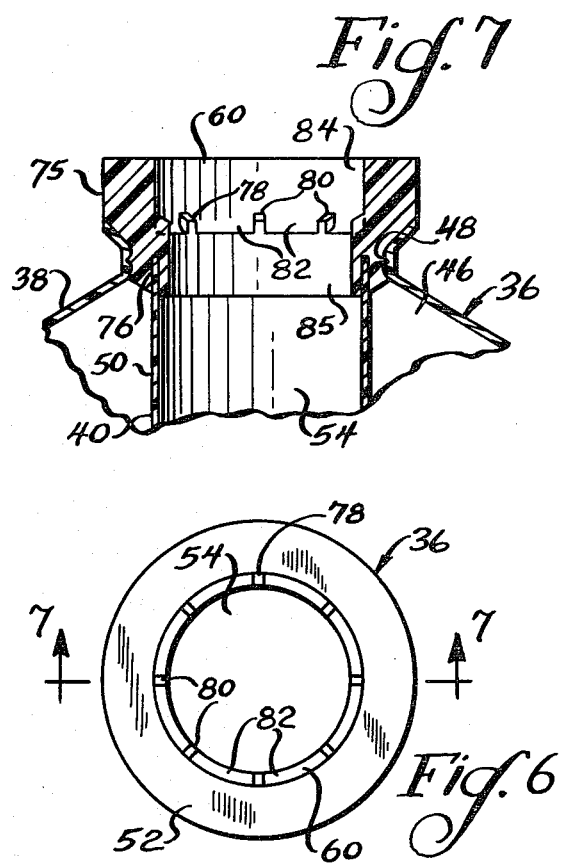
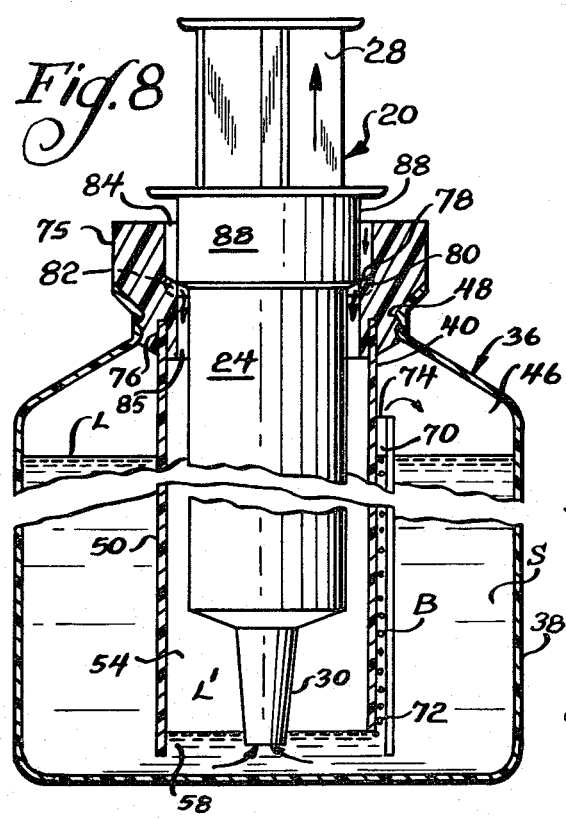
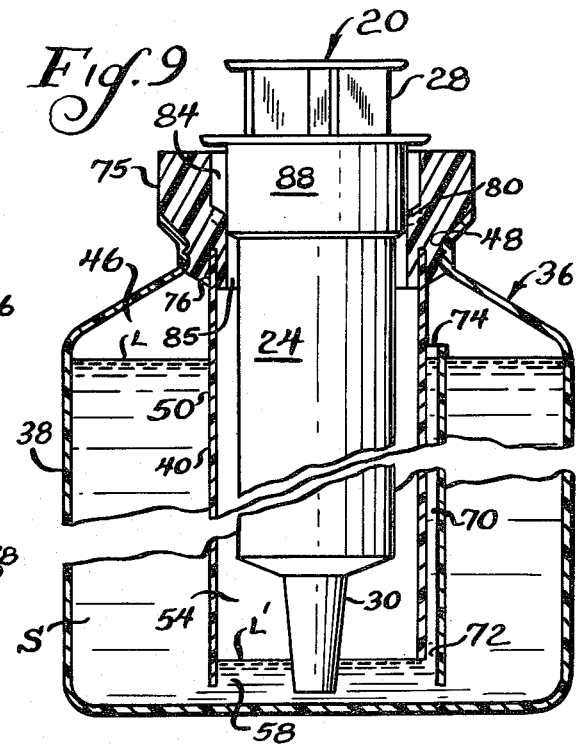

IRRIGATION SOLUTION DEVICE

BACKGROUND OF THE INVENTION

The present invention relates to solution containers, and more particularly to irrigation solution devices.

In general, the term "irrigation" connotes a procedure for delivering liquid to a body cavity, an indwelling tube, a wound, or other needed area. One of the more common of such procedures constitutes the irrigation of a Foley catheter during catheterization. Thus, it may be necessary to irrigate the catheter through its main lumen in order to remove blockage in the catheter lumen, or it may be desirable for other reasons to inject an irrigation solution through the catheter into the patient's bladder.

The normal procedure for irrigating a Foley catheter is described as follows. First, the junction of the catheter and a drainage tube connected to the proximal end of the catheter is prepped, and the upstream end of the drainage tube is then disconnected from the catheter. Next, a syringe is filled from a container retaining a sterile irrigation solution, and the tip of the syringe is inserted into the catheter lumen at the proximal end of the catheter. The user retains the proximal end portion of the catheter against the syringe tip by the fingers of one hand, while the other hand is utilized to pump the syringe and eject the fluid from the syringe into the catheter lumen. This procedure may be repeated a number of times in order to remove blockage from the catheter lumen or otherwise pump a sufficient volume of fluid into the patient's bladder. The syringe is refilled in the solution container between the successive pumping steps during which the syringe barrel may be placed in the solution itself. Since the irrigation procedure is normally undertaken without the use of sterile gloved hands, it is not uncommon that the physician or nurse carrying out the procedure may contact the syringe barrel with the ungloved hand resulting in contamination to the barrel of the syringe. Thus, when the syringe barrel is repositioned in the irrigation solution, the contaminated syringe barrel in turn contaminates the solution resulting in contaminated solution being drawn into the syringe. Thus, during each filling of the syringe, the solution may become more contaminated by the syringe barrel, and the contaminated solution is then introduced by the syringe into the catheter and the patient's bladder resulting in possible deleterious effects to the patient. Of course, the same problem may be present in other irrigation procedures where the syringe is repetitively filled from a solution container while the syringe barrel is immersed in the irrigation solution.

SUMMARY OF THE INVENTION

A principal feature of the present invention is the provision of an irrigation solution device of simplified construction and permitting irrigation in an improved manner.

The device of the present invention comprises a syringe having a barrel and a tip, and a container having sidewalls and a lower wall at least partially defining a solution receiving chamber, and an opening adjacent an upper portion of the container. The device has an elongated barrier member having wall means defining a channel to receive the syringe barrel and at least partially defining opening means adjacent an inner end of the barrier member. The barrier member is insertable through the container opening into an operative position with the inner end of the barrier member located adjacent the container lower wall. The channel has a width slightly larger than the syringe barrel to closely receive the syringe barrel while permitting passage of air between the atmosphere and the opening means, and the barrier member has a sufficient length to substantially cover the syringe barrel when positioned in the channel. The device has means for releasably closing an outer end portion of the barrier member, and means for sealingly engaging the barrier member to the container in the container opening responsive to insertion of the barrier member into the container.

A feature of the invention is that the container chamber may be readily filled with sterile solution while the barrier member is removed from the container.

A further feature of the present invention is that the barrier member may be inserted into the filled chamber with the closing means in place in order to seal the barrier member to the container in the container opening.

Another feature of the invention is that a partial vacuum is created in the container chamber at a location above the solution, thus preventing passage of more than a minimal amount of solution into the barrier member channel when the closing means is removed from the barrier member.

Another feature of the invention is that the closing means may be removed from the barrier member for access to the solution at the lower end of the barrier member channel.

Thus, a feature of the present invention is that the syringe barrel may be inserted into the barrier member channel in order to fill the syringe through the syringe tip without contact of the solution against the syringe barrel.

Another feature of the invention is that the syringe barrel may be repetitively filled in the barrier member channel while the exposed solution level remains at the lower end of the barrier member.

Thus, a feature of the invention is that the syringe barrel may be repetitively filled without contact of the solution against the syringe barrel, thus minimizing the possibility of contamination to the sterile irrigation solution by a contaminated syringe barrel.

Yet another feature of the invention is that the barrier member provides support for the syringe barrel while positioned in the barrier member channel.

A further feature of the invention is that the device may be provided with means for sealingly engaging an outer portion of the syringe barrel in order to close the barrier member channel from the atmosphere and permit prolonged storage of the syringe in the solution container between uses.

Further features will become more fully apparent in the following description of the embodiments of this invention and from the appended claims.

DESCRIPTION OF THE DRAWINGS

In the drawings:

FIG. 1 is a fragmentary perspective view illustrating use of a syringe for irrigating a catheter;

FIG. 2 is an elevational view, partly broken away, of an irrigation solution device of the present invention;

FIG. 3 is a sectional view of the device of FIG. 2;

FIG. 4 is a sectional view of the device of FIG. 3 during removal of a sealing member from a barrier member of the device;

FIG. 5 is a sectional view of the device of FIG. 4 illustrating use of the device to fill the syringe;

FIG. 6 is an end view of a barrier member for another embodiment of an irrigation solution device of the present invention;

FIG. 7 is a fragmentary sectional view taken substantially as indicated along the line 7—7 of FIG. 6;

FIG. 8 is a fragmentary sectional view of the device of FIGS. 6 and 7 illustrating use of the device during filling of the syringe; and FIG. 9 is a fragmentary sectional view of the device of FIG. 8 illustrating use of the device during storage of the syringe.

DESCRIPTION OF THE PREFERRED EMBODIMENTS

Referring now to FIG. 1, there is shown a syringe 20 of conventional type for irrigating a catheter 22 such as a Foley catheter, as shown. The syringe 20 has a barrel 24 defining a chamber 26 to receive the forward end of a plunger 28, or the syringe may have a compressible bulb connected to the barrel to effect pumping. The syringe 20 also has a tip 30 at its distal end communicating with the syringe chamber 26. In use, the syringe tip 30 is inserted into a drainage lumen 32 of the catheter 22 at a proximal end portion 34 of the catheter 22, after which the syringe is pumped to eject liquid from the syringe chamber 26 into the catheter lumen 32 and irrigate the catheter 22. Such a procedure is normally carried out without the use of sterile gloved hands, and, as will be appreciated from the drawing, the syringe barrel will likely become contaminated by the user's hands due to contact against the barrel. Thus, in the event that the syringe chamber 26 should be refilled by placement of the syringe barrel into the irrigation solution itself, the irrigation solution may become contaminated by the syringe barrel 24.

In accordance with the present invention, contact between the contaminated syringe barrel and the irrigation solution is prevented by an irrigation solution container, as will be described below. Thus, with reference to FIGS. 2-4, there is shown an irrigation solution device generally designated 36 having a container 38, and an insertable barrier member 40. The container 38 has side walls 42 and a lower wall 44 at least partially defining a solution receiving chamber 46. In addition, the container 38 has a port 48 defined by an upper portion of the container of reduced dimensions, with the port 48 communicating with the container chamber 46.

The barrier member 40 has an elongated inner cylindrical section 50, and an enlarged outer section 52, with the sections 50 and 52 defining an elongated channel 54 having a sufficient width to closely receive the syringe barrel 24 and a sufficient length to substantially cover the syringe barrel. As shown, the inner end section 50 of the barrier member 40 has an inner end portion 56 defining an opening 58 communicating between the channel 54 and container chamber 46 when the barrier member 40 is inserted into the container chamber. Also, the outer section 52 of the barrier member 40 defines an opening 60 communicating with the channel 54 at an outer end of the barrier member 40. In a preferred form, as shown, the inner end portion 56 of the barrier member 40 is spaced slightly from the lower wall 44 of the container 38 when the barrier member 40 is inserted into the container chamber 46. Alternatively, the inner end portion 56 of the barrier member 40 may contact the container lower wall 44 when the barrier member 40 is inserted into the container, and the inner section 50 of the barrier member 40 may have a side opening or openings communicating with the channel 54 adjacent the inner end portion 56 of the barrier member 40.

As shown, the barrier member 40 has a closure member 62 extending across and releasably covering the outer opening 60 of the barrier member 40. In a suitable form, the closure member 62 may comprise a sheet of flexible material adhered to the outer end section 52 of the barrier member 40 across the port or opening 60. Alternatively, the closure member 60 may comprise a plug releasably attached to the outer end section 52 of the barrier member 40, such that the plug may be selectively removed and secured to the barrier member 40, as desired. The barrier member 40 also has an annular resilient sealing member 64 secured to the barrier member 40 adjacent the outer end section 52, such that the sealing member 64 sealingly engages against the upper portion of the container 38 in the port 48 when the barrier member 40 is inserted into the container chamber 46, and the sealing member 64 prevents passage of air between the upper portion of the container chamber and the atmosphere through the port 48. Alternatively, the sealing member may be secured to the container 38 around the port 48, the barrier member 40 may be secured to the container through use of cooperating threads, the barrier member may be made from an elastic material, such as Kraton, a trademark of Shell Oil Company, such that the side surface of the one-piece barrier member sealingly engages against the container, or any other suitable construction, such that the barrier member 40 sealingly engages against the container when inserted into the container chamber 46 and secured in place. The sealing member 64 may be made of any suitable material, such as rubber.

The device 36 is supplied in a sterile condition to the user, such as at a hospital. In use, the barrier member 40 is removed from the container 38, and a sterile irrigation solution S may be poured through the container port 48 into the container chamber 46 until an upper level L of the solution S is attained below the location of the port 48, as illustrated in connection with FIG. 2. Next, the barrier member 40 containing the closure member 62 is inserted through the container port 48 into the container chamber 46 until the sealing member 64 makes sealing engagement with the container 38 around the port 48, thus closing the container chamber 46 from the atmosphere, as illustrated in connection with FIG. 3, and establishing a lower level L' to the solution S at the inner end portion 56 of the barrier member 40 adjacent the inner opening 58 of the barrier member channel 54. Next, with reference to FIG. 4, the closure member 62 is removed from the barrier member 40 in order to permit access to the barrier member channel 54 and the solution. As shown, a partial vacuum is created in the container chamber 46 above the upper level L of the solution S, thus preventing passage of the solution S more than a minimal distance into the barrier member channel 54, such that the lower level L' of the solution S in the barrier member channel 54 remains adjacent the inner opening 58 of the barrier member 40.

With reference to FIG. 5, the syringe 20 may be filled by inserting the syringe barrel 24 into the channel 54 of the barrier member 40 until the syringe tip 30 is positioned in the solution S below the barrier member opening 58. Next, the syringe plunger 28 is withdrawn from the barrel 24 in order to draw sterile irrigation solution S into the syringe chamber 26. During this time, the barrier member 40 serves as a support for the syringe barrel 24, and air passes from the atmosphere through the channel 54 intermediate the syringe barrel 24 and the barrier member sidewalls. Thus, the air passes through the barrier member opening 58 and forms bubbles B which pass toward the upper portion of the container chamber 46 in order to relieve the vacuum somewhat above the upper level L as the solution S lowers in the container chamber 46 and passes through the syringe tip 30 into the syringe chamber 26, as indicated by the direction of the arrows in the drawing.

When the syringe chamber 26 has been completely filled, the syringe 20 is removed from the barrier member 40 in order to perform the irrigation procedure in a manner as previously described. Thus, with reference to FIG. 1, the syringe tip 30 is connected to the catheter 22, and the irrigation solution is pumped into the drainage lumen 32 of the catheter 22. As previously noted, the syringe barrel 24 may become contaminated by the user's fingers at this time due to contact against the syringe barrel. After the irrigation solution has been pumped from the syringe 20, the syringe tip 30 is removed from the proximal end portion 34 of the catheter 22, and the syringe may be repositioned in the barrier member 40 of the device 36, as previously described in connection with FIG. 5. Again, the syringe barrel may be filled with the solution S while the lower level L' of the solution S remains at the inner end of the barrier member channel 54 adjacent the inner opening 58, such that the device prevents contact of the sterile irrigation solution S against the contaminated syringe barrel 24. Accordingly, the syringe 20 may be repetitively filled without contact of the contaminated syringe barrel against the sterile irrigation solution S, thus preventing contamination of the irrigation solution S by the syringe barrel, and permitting irrigation of the catheter 22 in an aseptic manner while minimizing the possibility of ejecting contaminated solution through the catheter into the patient's bladder.

After irrigation of the catheter has been completed, the closure member may be replaced on the outer end section 52 of the barrier member 40 in order to close the barrier member 40 and retain the sterile irrigation solution for subsequent use, if desired. Alternatively, the solution container 38 may be discarded at this time.

Another embodiment of the present invention is illustrated in FIGS. 6-9, in which like reference numerals designate like parts. In this embodiment, the barrier member 40 defines an elongated passageway 70 having an inner end 72 communicating with the barrier member channel 54 at a location spaced slightly above the inner opening 58 of the barrier member 40, and an outer end 74 communicating with an upper portion of the container chamber 46 above the upper level L of the solution S. Thus, the solution S assumes a lower level L' in the barrier member channel 54 adjacent the inner end 72 of the passageway 70, and, during filling of the syringe, air passes from the barrier member channel 54 through the passageway 70 to the upper end of the container chamber 46, rather than around the outside of the barrier member walls.

In this embodiment, the outer end portion of the barrier member 40 may comprise a resilient plug 75 of suitable material, such as rubber, which sealingly engages against the upper end portion of the container 38 in the port 48 when the barrier member 40 is inserted into the container chamber 46. In addition, the inner end portion of the plug 75 may have an annular slot 76 to receive an outer end portion of a cylindrical inner section 50 of the barrier member 40.

As best shown in FIGS. 6 and 7, the resilient plug 75 of the barrier member 40 has a ledge 78 defined by a plurality of upstanding flanges 80 spaced circumferentially about the ledge 78, such that the ledge flanges 80 define a plurality of apertures 82 which communicate between outer and inner portions 84 and 85 of the channel 54, respectively, relative the ledge 78.

With reference to FIGS. 8 and 9, the syringe 20 has an annular enlargement 88 adjacent a proximal end of the syringe barrel 24. As shown, the inside dimensions of the outer channel portion 84 are slightly larger than the annular enlargement 88 of the syringe barrel 24, while the inside dimensions of the inner channel portion 85 in the plug 75 are slightly less than the outer dimensions of the syringe enlargement 88. Thus, with reference to FIG. 8, when the syringe 20 is placed in the barrier member channel 54, the barrel enlargement 88 normally rests upon the ledge 78 of the plug 75 at a first outer position of the syringe. In this configuration, the syringe barrel and enlargement 88 are spaced from the barrier member apertures 82, such that air from the atmosphere is permitted to pass through the apertures 82 into the inner portion 85 of the barrier member channel 54 during filling of the syringe. Accordingly, when the syringe plunger 28 is withdrawn from the syringe barrel 24, air passes from the atmosphere through the apertures 82 into the inner portion of the barrier member channel 54, after which the air passes through the passageway 70 into the upper portion of the container chamber 46, in order to permit filling of the syringe chamber without contact of the irrigation solution S against the syringe barrel 24.

After use of the syringe 20 has been completed during the irrigation procedure, the syringe 20 may be moved from its first outer position in the barrier member 40, as illustrated in FIG. 8, to an inner second position, as illustrated in FIG. 9. In this configuration, the syringe enlargement 88 sealingly engages against the inside surface of the resilient plug 75 in the inner portion 85 of the plug channel 54, thus preventing passage of air through the apertures 82 and closing the inner portion of the barrier member channel 54 from the atmosphere. Accordingly, the irrigation solution S in the container chamber 46 may be closed to the atmosphere to prevent contamination of the sterile solution and permit storage of the device during extended periods of time until desired for further use.

The foregoing detailed description is given for clearness of understanding only, and no unnecessary limitations should be understood therefrom, as modifications will be obvious to those skilled in the art.

I claim:

1. An irrigation solution device, comprising:
a syringe having a barrel and a tip;
a container having sidewalls and a lower wall defining a solution receiving chamber, and an opening adjacent an upper portion of the container, said chamber containing a sterile irrigation solution;
an elongated barrier member having a first outer opening, an inner end portion defining a second opening, and a channel to receive said syringe, said barrier member being insertable through the container opening into an operative position with the inner end portion of the barrier member located adjacent the container lower wall and with said second opening of the barrier member communicating with the container chamber, said channel having a width slightly larger than the syringe barrel to closely receive the syringe barrel while permitting passage of air between the atmosphere and the second opening, said barrier member having a sufficient length to substantially cover the syringe barrel when positioned in said channel, said barrier member being removed from the container and said syringe being removed from the barrier member with said barrier member having a closure member releasably attached to an outer end portion of the barrier member and closing said second opening of the barrier member from the atmosphere; and means for sealingly engaging the barrier member to the container in said container opening responsive to insertion of the barrier member into the container to said operative position, whereby said barrier member may be inserted into the container to said operative position with the inner end portion of the barrier member in said solution and with said closure member attached to the barrier member to form an air column in the barrier member channel and a lower level of the solution adjacent said second opening, the closure member may be removed from the barrier member to expose said channel, and said syringe may be inserted into the channel to form a sterile solution containing device.

2. The device of claim 1 including means defining a passageway communicating between a lower portion of the channel and an upper portion of the chamber exterior the barrier member relative to the channel.

3. The device of claim 1 including means for releasably closing the channel responsive to insertion of the syringe into the channel.

4. An irrigation solution device, comprising:
a syringe having a barrel and a tip;
a container having sidewalls and a lower wall at least partially defining a solution receiving chamber, and an opening adjacent an upper portion of the container;
an elongated barrier member having wall means defining a channel to receive the syringe barrel and at least partially defining opening means adjacent an inner end of the barrier member, said barrier member being insertable through the container opening into an operative position with the inner end of the barrier member located adjacent the container lower wall, said channel having a width slightly larger than the syringe barrel to closely receive the syringe barrel while permitting passage of air between the atmosphere and said opening means, and said barrier member having a sufficient length to substantially cover the syringe barrel when positioned in said channel;
means for releasably closing an outer end portion of the barrier member;
means for sealingly engaging the barrier member to the container in said container opening responsive to insertion of the barrier member into the container; and
support means inside said channel for removably supporting the syringe at a location inside the channel at a first outer position of the syringe with the syringe tip adjacent the barrier member opening means while permitting passage of air from the atmosphere through the barrier member channel and opening means, and sealing means inside the channel for releasably sealing the syringe to an outer portion of the barrier member at a location inside the channel while closing an inner portion of the channel to the atmosphere at a second inner position of the syringe inserted into said barrier member relative to said first position.

5. The device of claim 4 wherein the closing means comprises a closure member releasably attached to an outer end of the barrier member and closing the channel from the atmosphere.

6. The device of claim 4 wherein the engaging means comprises a resilient sealing member positioned intermediate the barrier member and container in the container opening.

7. The device of claim 4 wherein the engaging means comprises a resilient outer end portion of the barrier member.

8. The device of claim 4 wherein said wall means defines passageway means having an inner end communicating with an inner end of the channel spaced outwardly relative the opening means, and having an outer end communicating with an upper portion of the chamber when said barrier member is in said operative position.

9. The device of claim 4 wherein said wall means defines said opening means at the inner end of the barrier member, and in which said inner end of the barrier member is spaced from the container lower wall when said barrier member is in said operative position.

10. The device of claim 4 wherein said wall means has an inner cylindrical section.

11. The device of claim 4 wherein said barrier member has an outer end defining an enlarged portion of the channel.

12. An irrigation solution device, comprising:
a syringe having a barrel and a tip;
a container having sidewalls and a lower wall at least partially defining a solution receiving chamber, and an opening adjacent an upper portion of the container;
an elongated barrier member having wall means defining a channel to receive the syringe barrel and at least partially defining opening means adjacent an inner end of the barrier member, said barrier member being insertable through the container opening into an operative position with the inner end of the barrier member located adjacent the container lower wall, said channel having a width slightly larger than the syringe barrel to closely receive the syringe barrel while permitting passage of air between the atmosphere and said opening means, and said barrier member having a sufficient length to substantially cover the syringe barrel when positioned in said channel;
means for releasably closing an outer end portion of the barrier member;
means for sealingly engaging the barrier member to the container in said container opening responsive to insertion of the barrier member into the container; and
means for releasably sealing the syringe to an outer portion of the barrier member and closing an inner portion of the channel to the atmosphere, said sealing means comprising an annular enlargement on an outer portion of the syringe barrel and a ledge on an outer portion of the barrier member having aperture means communicating between opposed inner and outer portions of the channel relative said ledge, said syringe enlargement resting on said ledge when the syringe is located at a first position in the channel with air passing between the atmosphere through the aperture means to said opening means, and said syringe enlargement sealingly engaging against the barrier member inwardly of said ledge to close an inner portion of said channel from the atmosphere when said syringe is inserted to a second sealing position in the barrier member inwardly relative said first position.

* * * * *